United States Patent [19]

Carr et al.

[11] 4,357,078
[45] Nov. 2, 1982

[54] LIQUID CRYSTAL COMPOUNDS CONTAINING AN ALICYCLIC RING AND EXHIBITING A LOW DIELECTRIC ANISOTROPY AND LIQUID CRYSTAL MATERIALS AND DEVICES INCORPORATING SUCH COMPOUNDS

[75] Inventors: Neil Carr, Hull; George W. Gray, Cottingham; Stephen M. Kelly, Hull, all of England

[73] Assignee: The Secretary of State for Defence in Her Britannic Majesty's Government of the United Kingdom of Great Britain and Northern Ireland, London, England

[21] Appl. No.: 228,979

[22] Filed: Jan. 27, 1981

[30] Foreign Application Priority Data

Jan. 30, 1980 [GB] United Kingdom ................. 8003129
Jun. 27, 1980 [GB] United Kingdom ................. 8021068
Dec. 2, 1980 [GB] United Kingdom ................. 8038553

[51] Int. Cl.$^3$ .......................... G02F 1/13; C09K 3/34; C07C 43/21; C07C 43/225
[52] U.S. Cl. .................. 350/350 R; 252/299.62; 252/299.63; 260/463; 560/138; 568/631; 568/632; 568/633; 568/634; 568/644; 568/645; 568/647
[58] Field of Search ................. 350/350 R; 252/299.6, 252/299.62, 299.63, 299.5; 260/463; 560/138; 568/632, 633, 634, 644, 645, 647, 631

[56] References Cited

U.S. PATENT DOCUMENTS

| | | | |
|---|---|---|---|
| 4,035,056 | 7/1977 | Coates et al. | 252/299.66 |
| 4,113,647 | 9/1978 | Coates et al. | 252/299.62 |
| 4,130,502 | 12/1978 | Eidemschink et al. | 252/299.63 |
| 4,154,697 | 5/1979 | Eidemschink et al. | 252/299.63 |
| 4,219,256 | 8/1980 | Gray et al. | 252/299.62 |
| 4,229,315 | 10/1980 | Krause et al. | 252/299.63 |
| 4,261,651 | 4/1981 | Gray et al. | 252/299.62 |
| 4,261,652 | 4/1981 | Gray et al. | 252/299.62 |

FOREIGN PATENT DOCUMENTS

| | | | |
|---|---|---|---|
| 23728 | 2/1981 | European Pat. Off. | 252/299.63 |
| 30761 | 6/1981 | European Pat. Off. | 252/299.63 |
| 3023368 | 12/1981 | Fed. Rep. of Germany | 252/299.63 |
| 105701 | 5/1974 | German Democratic Rep. | 252/299.63 |
| 56-43386 | 4/1981 | Japan | 252/299.63 |
| 2063287 | 6/1981 | United Kingdom | 252/299.63 |

OTHER PUBLICATIONS

Gray, G. W., Mol. Cryst. Liq. Cryst., vol. 63, pp. 3-18 (1981); presented at the 8th International L. C. Conf., Kyoto, Japan, Jun. 30-Jul. 4, 1980.

Gray, G. W. et al., Mol. Cryst. Liq. Cryst., vol. 53, pp. 147-166 (1979).

Demus, D., Nonemissive Electrooptic Displays, pp. 83-119 (1975).

*Primary Examiner*—Teddy S. Gron
*Attorney, Agent, or Firm*—Stevens, Davis, Miller & Mosher

[57] ABSTRACT

Novel liquid crystal compounds exhibiting a low dielectric anisotropy have a structural formula:

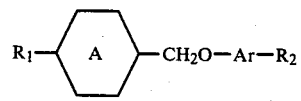

where $R_1$ is an alkyl group, $R_2$ is a group containing an alkyl group R and is either an alkyl group R, an alkoxy group OR, an alkylcarbonyloxy group OCOR or an alkoxycarbonyloxy group OCOOR, $R_1$ and R containing up to 18 carbon atoms,

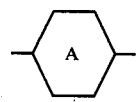

is a trans-1,4-disubstituted cyclohexane ring or a 1,4-disubstituted bicyclo(2,2,2)octane ring and Ar is a 1,4 disubstituted benzene ring

, a 3-fluoro-1,4 disubstituted benzene ring or a 2,6 disubstituted naphthalene ring

These compounds may be used in liquid crystal mixture compositions for use in a number of known electro-optic effects.

The compounds may be prepared by routes in which the individual steps involved are known.

10 Claims, 7 Drawing Figures

LIQUID CRYSTAL COMPOUNDS CONTAINING AN ALICYCLIC RING AND EXHIBITING A LOW DIELECTRIC ANISOTROPY AND LIQUID CRYSTAL MATERIALS AND DEVICES INCORPORATING SUCH COMPOUNDS

The present invention relates to liquid crystal compounds containing an alicyclic ring and exhibiting a low (small) dielectric anisotropy and liquid crystal materials and devices incorporating such compounds.

The use of liquid crystal materials to exhibit electro-optic effects in display devices such as digital calculators or watches is now well known. One of the parameters of a liquid crystal material which is important in relation to electro-optical operation is the dielectric anisotropy ($\Delta\epsilon$) of the material. This is the difference, for a given frequency and temperature, between the average dielectric constant measured parallel ($\epsilon_\parallel$) to the molecules of the material, e.g. when aligned together, less the average dielectric constant measured perpendicular ($\epsilon_\perp$) to the molecules.

The sign and magnitude of the dielectric anisotropy of a given liquid crystal material is one of the major parameters which determine the kinds of electro-optic devices in which that material may be used.

For example, materials having a positive dielectric anisotropy, herein referred to as 'positive' materials, e.g. mixtures of 4-alkyl-or-alkoxy-4'-cyanobiphenyls and a 4''-alkyl-or-alkoxy-4-cyano-p-terphenyl may be used in known twisted nematic effect devices (if nematic) or known cholesteric-to-nematic phase change effect devices (if cholesteric) in which the molecular arrangement is changed from the focal conic to the homeotropic texture.

Materials having a negative dielectric anisotropy herein referred to as 'negative' materials (of suitable resistivity) may be used in known dynamic scattering effect devices (if nematic) or cholesteric memory mode devices (if cholesteric).

Materials having a low (e.g. $\Delta\epsilon$ less than 1) dielectric anisotropy may also be mixed with those having a positive or negative dielectric anisotropy to produce mixtures whose overall dielectric anisotropy is positive (but reduced in value).

According to the present invention in a first aspect there is provided a novel liquid crystal compound exhibiting a low dielectric anisotropy having a structural formula:

formula (I)

where $R_1$ is an alkyl group; $R_2$ is a group containing an alkyl group R and is either an alkyl group R, or an alkoxy group OR, an alkylcarbonyloxy group OCOR or an alkoxycarbonyloxy group OCOOR, $R_1$ and R containing up to 18 carbon atoms;

is a trans-1,4-disubstituted cyclohexane ring, or a 1,4-disubstituted bicyclo(2,2,2)octane ring; and Ar is a 1,4-disubstituted benzene ring, a 3-fluoro-1,4-disubstituted benzene ring, or a 2,6 disubstituted naphthalene ring.

The alkyl groups $R_1$ and R preferably contain ten or less carbon atoms and may be normal or branched. If branched one or both of these alkyl groups may contain a chiral centre in which case the compound may be optically active. Preferably $R_1$ is an n-alkyl group containing up to 10 carbon atoms and $R_2$ is an n-alkyl or n-alkoxy group containing up to 10 carbon atoms.

By a 'liquid crystal compound' is meant a compound in one of the following two known categories:
  i Compounds which normally exhibit a liquid crystal phase;
  ii Compounds which do not normally exhibit a liquid crystal phase but which nevertheless usefully affect some aspect of liquid crystal behaviour when dissolved in other liquid crystal compounds.

Compounds in category (ii) show a 'monotropic' or a 'virtual' liquid crystal to isotropic liquid transition at a temperature below the melting point of their solid phase. The monotropic or virtual transition may be detected respectively by rapid cooling of the liquid phase or by dissolving the compound in a material exhibiting a liquid crystal phase, observing the change in the transition to the isotropic liquid phase of the material by the addition and calculating the virtual transition temperature by extrapolation.

Compounds in category (ii) might for example be usefully dissolved in other liquid crystal compounds to extend or vary the liquid crystal temperature ranges of the compounds or to vary the molecular helical pitch (in the case of cholesteric liquid crystals).

One or more compounds according to formula (I) may be used in any of the following applications:
  (i) Together with a positive nematic material giving an overall positive nematic material for use in twisted nematic effect devices particularly multiplexed devices; an example of such a device is given below.
  (ii) Either alone (if $\Delta\epsilon$ is large and negative), or together with another nematic material, preferably negative, giving an overall negative material (e.g. if $\Delta\epsilon$ is small), preferably also with a pleochroic dye, in Freedericksz effect devices in which the molecular arrangement may be changed from the homeotropic texture (OFF state) to the homogeneous texture (ON state); an example of such a device is given below.
  (iii) Together with a nematic material giving an overall positive nematic material, preferably also with a pleochroic dye, in Freedericksz effect devices in which the molecular arrangement may be changed from the homogeneous texture (OFF state) to the homeotropic texture (OFF state) by an electric field.
  (iv) Together with an optically active material giving an overall negative material which is a cholesteric of suitable resistivity (about $10^9$ ohm-cm), in cholesteric memory mode devices in which the molecular arrangement may be changed from a twisted homogeneous texture (OFF state) to a turbulent scattering focal conic texture (ON state) by an electric field.

(v) Together with an optically active material giving an overall negative material which is a cholesteric, preferably together also with a pleochroic dye, in cholesteric-to-nematic phase change effect devices in which the molecular arrangement may be changed from a weakly scattering surface aligned homeotropic texture (OFF state) to a strongly scattering twisted homogeneous texture (ON state) by an electric field.

(vi) Together with an optically active material giving an overall positive material which is a cholesteric, preferably together also with a pleochroic dye, in cholesteric-to-nematic phase change effect devices in which the molecular arrangement may be changed from a scattering focal conic texture (OFF state) to a clear homeotropic texture (ON state) by an electric field.

(vii) Together with a nematic material giving an overall negative nematic material of suitable resistivity (about $10^9$ ohm-cm), in dynamic scattering effect devices in which the molecular arrangement may be changed from a clear homeotropic texture (OFF state) to a turbulent scattering texture (ON state) by an electric field.

(viii) Together with a positive nematic material giving an overall positive nematic material in two frequency switching effect devices in which the dielectric anisotropy of the material may be changed from (at low frequency) positive (OFF state) to negative (ON state) by the application of a high frequency electric field.

The construction and operation of the above devices and the general kinds of material which are suitable for use in them are themselves known.

It will be apparent to those skilled in the art that in the above application where mixtures are formed these mixtures can have the value and sign of their dielectric anisotropy controlled as required by control of the proportions of the materials blended together to form them.

Where a material is added to one or more compounds according to formula (I) the material may itself be a mixture of 2 or more compounds.

Mixtures may be formed in a known way, e.g. simply by heating the constituent compounds to form an overall isotropic liquid, stirring the liquid and allowing it to cool.

The compounds according to formula (I) may usefully reduce operating voltages in the above applications as well as enhance negativity or reduce positivity of the dielectric anisotropy; this may usefully affect other properties, e.g. multiplexability in twisted nematic effect devices or switching frequency in two-frequency switching effect devices.

According to the present invention in a second aspect there is provided a mixture of liquid crystal compounds including at least one compound according to formula (I) above. Such a mixture may, depending on its selected composition and properties, be used in any one of the applications (i) to (viii) above.

An example of a mixture according to the second aspect which may be used in multiplexed twisted nematic devices is one including, in addition to at least one compound according to formula (I) above, one or more 4'-alkyl- or 4'-alkoxy-4-cyanobiphenyls and one or more of the following compounds:

(II)

(III)

(IV)

(V)

(VI)

(VII)

R = alkyl

Preferably the 4'-alkyl- or 4'-alkoxy-4-cyanobiphenyls constitute between about 10 and 90% by weight of the mixture and the compounds selected from formulae (II) to (VII) constitute not more than about 20% by weight in total, the remainder being one or more compounds, according to formula (I) above.

Preferably each 4'-alkyl- or 4'-alkoxy-4-cyanobiphenyl incorporated in the mixture has five or less carbon atoms in its alkoxy or alkyl group. Preferably this number of carbon atoms is odd when the group is an alkoxy group and is even when the group is an alkyl group.

As further examples, the mixture according to the second aspect may be a compound according to formula (I) above mixed together with one or more compounds in the following known families for use in one or more of the applications given above (the actual application(s) depending on the mixture properties):

(i)

(ii)

(iii)

(iv)

where (vii) [cyclohexane ring figure]

is a cyclohexane ring, (viii) [bicyclooctane ring figure]

is a bicyclo(2,2,2)octane ring, X is a 1,4 phenylene group (x) [phenylene figure], or a 4,4' biphenyl group (xii) [biphenyl figure], or a 2,6 naphthyl group (xiv) [naphthyl figure];

and Y is CN, or R', or OR' or CO.O—X—Y' where Y' is CN, or R' or OR'; the definition of R' being the same as that of R.

According to the present invention in a third aspect a liquid crystal display device includes two dielectric substrates at least one of which is optically transparent, a layer of liquid crystal material sandwiched between the substrates and electrodes on the inner surfaces of the substrates to enable an electric field to be applied across the layer of liquid crystal material to provide an electro-optic effect therein, characterised in that the liquid crystal material consists of or includes a compound according to formula (I) above.

The device according to the third aspect may be a twisted nematic effect device, which may or may not be operated in a multiplexed fashion, a cholesteric-to-nematic phase change effect device, a Freedericksz effect device, a two-frequency switching effect device, a cholesteric memory mode device or a dynamic scattering effect device all constructed in a known manner. The various ways in which compounds according to formula (I) may be used in these devices are outlined above and will be further apparent to those skilled in the art.

Examples of the preparation and properties of compounds according to formula (I) above will now be given.

EXAMPLE 1

This example describes the preparation of 4-(trans-4'-alkylcyclohexylmethoxy)-alkylbenzenes and 4-(trans-4'-alkyl cyclohexylmethoxy)-alkoxybenzenes by the following route:

where
$R_1$ is an alkyl group and Y is an alkyl or alkoxy group.

STEP A1:
The production of trans-4-alkylcyclohexylmethanols.

STEP B1:
The production of trans-4-alkylcyclohexylmethyl bromides.

STEP C1:
The production of 4-(trans-4'-alkylcyclohexylmethoxy)-alkylbenzenes or 4-(trans-4'-alkylcyclohexylmethoxy)-alkoxybenzenes.

An example of this preparation will now be given for the case where $R_1$ is ethyl to illustrate the procedure. (The same procedure is also used in cases where $R_1$ is other than ethyl).

STEP A1
The production of trans-4-ethylcyclohexylmethanol from the known trans-4-ethylcyclohexane-1-carboxylic acid.

Trans-4-ethylcyclohexane-1-carboxylic acid (10.9 g, 0.07 mole) is added to thionyl chloride (120 cm$^3$) and the mixture heated under reflux for 90 min. The excess of thionyl chloride is removed from the cooled solution in vacuo. Ether (50 cm$^3$ of sodium-dried) is then added to the residue and the solvent is distilled off again in vacuo. This procedure is carried out twice to remove the last traces of thionyl chloride. A solution of the acid chloride in ether (100 cm$^3$ of sodium-dried) is added over 1 hr to a suspension of lithium aluminium hydride (3.42 g, 0.09 mole) in ether (80 cm$^3$ of sodium-dried); after the addition, the whole is then heated under reflux for 20 min. Water (8 cm$^3$) is added dropwise, slowly and cautiously, to the cooled solution to destroy the excess of lithium aluminium hydride; sulphuric acid (100 cm$^3$ of aqueous 10%) is then added slowly to the mixture. The aqueous layer is shaken with ether (3×80 cm$^3$); the combine ethereal extracts are washed with water (100 cm$^3$ and 50 cm$^3$) and dried over sodium sulphate. The required alcohol is then obtained by removing the ether in vacuo and distilling the product under reduced pressure. The yield of trans-4-ethylcyclohexylmethanol is 8.95 g (90%), bp 140° C. at 3 mm Hg.

STEP B1
The production of trans-4-ethylcyclohexylmethyl bromide from trans-4-ethylcyclohexylmethanol.

To a stirred solution of aqueous hydrobromic acid (15 cm$^3$ of 48–50%), concentrated sulphuric acid (4 cm$^3$), and trans-4-ethylcyclohexylmethanol (9.94 g, 0.07 mole) is added dropwise an additional amount of concentrated sulphuric acid (2.5 cm$^3$). The whole is then heated under reflux for 3 hr, cooled, poured onto ice (60 g) and shaken with ether (3×60 cm$^3$). The combined ethereal extracts are washed with water (3×60 cm$^3$), an equal volume of concentrated hydrochloric acid, water (3×60 cm$^3$), sodium bicarbonate (3×60 cm$^3$ of an aqueous 5% solution), and saturated sodium chloride solution (3×60 cm$^3$). The solution of the bromide is dried (CaCO$_3$), the solvent removed in vacuo, and the crude bromide distilled under reduced pressure. The yield of trans-4-ethylcyclohexylmethyl bromide is 12.1 g (84%), bp 140° C. at 15 mm Hg.

STEP C1
The production of 4-(trans-4'-ethylcyclohexylmethoxy)-alkyl- or -alkoxy-benzenes.

The trans-4-ethylcyclohexylmethyl bromide (0.01 mole) is added to the appropriate 4-alkyl- or 4-alkoxy-phenol (0.015 mole) and potassium hydroxide (0.0175 mole) in aqueous solution of 2-ethoxyethanol (5 cm$^3$ of 95%). The mixture is then heated under reflux for 2 hr, whereupon solid potassium hydroxide (0.0025 mole) is added and the mixture is again left under reflux for 2 hr. The reaction mixture is poured into water (100 cm$^3$) and the whole is shaken with ether (3×80 cm$^3$). The ethereal extracts are washed with aqueous sodium hydroxide (3×60 cm$^3$ of 20%), water (3×80 cm$^3$), and dried (Na$_2$SO$_4$). The crude material is then column chromatographed using silica gel as the stationary phase and a 2:1 mixture of chloroform:light petrol (bp 40°–60° C.) is used as the eluant. The final product is then obtained by distillation under reduced pressure, or by crystallisation if the compound has a melting point equal to or greater than 30° C. (using solid carbon dioxide as refrigerant).

Examples of products of Example 1 are given in Tables 1 and 2 as follows:

TABLE 1

Compounds of the form $R_1$—(H)—CH$_2$O—(◯)—OR

| | | $R_1$, R as defined above | | |
|---|---|---|---|---|
| $R_1$ | R | C-I | $S_B$-N/I | N-I |
| n-C$_3$H$_7$ | C$_2$H$_5$ | 73° | — | [44°] |
| n-C$_3$H$_7$ | n-C$_4$H$_9$ | 55 | — | (46) |
| n-C$_5$H$_{11}$ | CH$_3$ | 46 | — | (38) |
| n-C$_5$H$_{11}$ | n-C$_4$H$_9$ | 55 | (47) | (53) |
| n-C$_6$H$_{13}$ | CH$_3$ | 45 | — | [30] |
| n-C$_6$H$_{13}$ | n-C$_4$H$_9$ | 54 | (50) | — |
| n-C$_3$H$_7$ | CH$_3$ | 42 | — | [23] |
| n-C$_3$H$_7$ | n-C$_3$H$_7$ | 53 | — | (34) |
| n-C$_3$H$_7$ | n-C$_5$H$_{11}$ | 54 | — | (42) |
| n-C$_3$H$_7$ | n-C$_6$H$_{13}$ | 52 | (49) | — |
| n-C$_3$H$_7$ | n-C$_7$H$_{15}$ | 60 | — | [50] |
| CH$_3$ | n-C$_4$H$_9$ | 55 | — | [18] | where [] represents a virtual transition temperature and ( ) represents a monotropic transition temperature
also where
C-I represents crystalline solid-to-isotropic liqiud transition temperature (°C.)
$S_B$-N represents Smectic B-to-nematic liqiud crystal transition temperature (°C.)
$S_B$-I represents Smectic B-to-isotropic liqiud transition temperature (°C.)
N-I represents nematic-to-isotropic liqiud transition temperature (°C.)

TABLE 2

Compounds of the form:

R₁—◯—CH₂O—◯—R    R₁ and R as defined above

| R₁ | R | C-I | N-I |
|---|---|---|---|
| n-C₃H₇ | n-C₅H₁₁ | 24 | [ 5] |
| n-C₅H₁₁ | CH₃ | 47 | [17] |
| n-C₅H₁₁ | C₂H₅ | 30 | [ 4] |
| n-C₅H₁₁ | n-C₃H₇ | 32 | [ 4] |
| n-C₅H₁₁ | n-C₄H₉ | 17 | [−4 ] |
| n-C₅H₁₁ | n-C₅H₁₁ | 35 | [21] |
| n-C₅H₁₁ | n-C₆H₁₃ | 35 | [18] |
| n-C₅H₁₁ | n-C₇H₁₅ | 38 | [26] |

[ ]represents a virtual transition temperature;
C-I etc as above

EXAMPLE 2

This example describes the preparation of 4-(4'-alkyl-1'-bicyclo(2,2,2)octylmethoxy)-alkylbenzenes and 4-(4'-alkyl-1'-bicyclo(2,2,2)octylmethoxy)-alkoxybenzenes by the following route:

where
R₁ is an alkyl group and Y is an alkyl or alkoxy group.

STEP A2:
The production of 4-alkyl-1-bicyclo(2,2,2)octylmethanols.

STEP B2:
The production of 4-alkyl-1-bicyclo(2,2,2)octylmethyl toluene-4-sulphonates.

STEP C2:
The production of 4-(4'-alkyl-1'-bicyclo(2,2,2)octylmethoxy)-alkylbenzenes or 4-(4'-alkyl-1'-bicyclo(2,2,-2)octylmethoxy)-alkoxybenzenes.

An example of this route will now be given for R₁=n-pentyl.

STEP A2

The production of 4-n-pentyl-1-bicyclo(2,2,2)octyl-methanol from the known 4-n-pentylbicyclo(2,2,2)octane-1-carboxylic acid.

This step is identical to STEP A1 above, using here the known 4-n-pentylbicyclo(2,2,2)octane-1-carboxylic acid (2.6 g, 0.0116 mole) (see UK patent application No. 32351/78). The yield of 4-n-pentyl-1-bicyclo(2,2,2)octylmethanol is 2.2 g (90%), bp 110° C. at 0.5 mm Hg.

STEP B2

The production of 4-n-pentyl-1-bicyclo(2,2,2)octyl-methyl toluene-4-sulphonate from 4-n-pentyl-1-bicyclo(2,2,2)octylmethanol.

4-n-Pentyl-1-bicyclo(2,2,2)octylmethanol (2.5 g, 0.0119 mole) is heated at 40° C. in pyridine (33 cm³ of sieve-dried) with toluene-4-sulphonyl chloride (3.4 g, 0.0179 mole) with stirring for 60 hr. The reaction mixture is poured into iced-water (60 cm³) and the product extracted into ether (3×50 cm³). The combined ethereal extracts are washed with dilute hydrochloric acid (50 cm³), water (3×50 cm³), and dried (CaCO₃). The solvent is removed in vacuo and the crude tosylate crystallised from light petroleum (bp 40°–60° C.). The yield of 4-n-pentyl-1-bicyclo(2,2,2)octylmethyl toluene-4-sulphonate is 3.1 g (71%), mp 67° C.

STEP C2

The production of 4-(4'-alkyl-1'-bicyclo(2,2,2)octyl-methoxy)-alkylbenzenes or 4-(4'-alkyl-1'-bicyclo(2,2,-2)octylmethoxy)-alkoxybenzenes from 4-alkyl-1-bicyclo(2,2,2)octylmethyl toluene-4-sulphonates.

4-Alkyl-1-bicyclo(2,2,2)octylmethyl toluene-4-sulphonate (0.007 mole) and potassium carbonate (2.9 g, 0.021 mole) are heated under reflux in dimethylformamide (12.5 cm³ of sieve-dried) for 16 hr with the required 4-alkyl- or 4-alkoxy-phenol (0.21 mole), with stirring. The reaction mixture is poured into water (60 cm³) and the organic product extracted into ether (3×60 cm³). The combined ethereal extracts are washed with aqueous sodium hydroxide (3×60 cm³ of 20%), water (2×60 cm³), and dried (Na₂SO₄). The solvent is removed in vacuo and the crude product column chromatographed using silica gel as the stationary phase and a 2:1 (v:v) mixture of chloroform:light petroleum (bp 40°–60° C.) as the eluant. The final product is obtained by distillation under reduced pressure. Examples of products of Step C2 are given in Table 3 as follows:

Compounds of the form:

R₁—◯—CH₂O—◯—R₂

| R₁ | R₂ | C-I (°C.) | S_B-N (°C.) | N-I (°C.) |
|---|---|---|---|---|
| n-C₃H₇ | n-C₅H₁₁ | 51 | | [21] |
| n-C₅H₁₁ | CH₃ | 69 | | [26] |
| n-C₅H₁₁ | C₂H₅ | 58 | | [20] |
| n-C₅H₁₁ | n-C₃H₇ | 56 | | [30] |
| n-C₅H₁₁ | n-C₄H₉ | 56 | | [22] |
| n-C₅H₁₁ | n-C₅H₁₁ | 47 | | (32) |
| n-C₅H₁₁ | n-C₆H₁₃ | 43 | | [27] |
| n-C₅H₁₁ | n-C₇H₁₅ | 47 | (35.5) | (36) |
| n-C₅H₁₁ | n-C₄H₉O | 74 | | [64] |

EXAMPLE 3

This example describes the preparation of 4-(trans-4'-alkylcyclohexylmethoxy)-3-fluoroalkylbenzenes and 6-(trans-4'-alkylcyclohexylmethoxy)-2-alkylnaphthalenes by the following route:

where, $R_1$ and $R_2$ are alkyl groups as defined above, is a trans-1,4-disubstituted cyclohexane ring, and Ar is a 3-fluoro-1,4-disubstituted benzene ring or a 2,6-disubstituted naphthalene ring.

STEP A3:

The production of trans-4-alkylcyclohexylmethanols

STEP B3:

The production of trans-4-alkylcyclohexylmethyl bromides.

STEP C3:

The production of 4-(trans-4'-alkylcyclohexylmethoxy)-3-fluoroalkylbenzenes and 6-(trans-4'-alkylcyclohexylmethoxy)-2-alkylnaphthalenes.

STEP A3:

This step may be carried out by the method of Step A1 described in the said UK application.

An example of such a product is trans-4-n-pentylcyclohexylmethanol, yield 90%, bp 150° C. at 3 mm Hg.

STEP B3:

The production of trans-4-alkylcyclohexylmethyl bromides from trans-4-alkylcyclohexylmethanols.

This step may be carried out by the method of Step B1 described above.

An example of such a product is trans-4-n-pentylcyclohexylmethyl bromide, yield 84%, bp 150° C. at 15 mm Hg.

STEP C3:

The production of 4-(trans-4'-alkylcyclohexylmethoxy)-3-fluoroalkylbenzenes and 6-(trans-4'-alkylcyclohexylmethoxy)-2-alkylnaphthalenes from trans-4-alkylcyclohexylmethyl bromides.

This step may be carried out essentially by the same method as Step C1 described above, (using the appropriate hydroxy compound instead of the 4-alkyl or 4-alkoxyphenols as in that Step C1.)

Examples of such products are

Yield, 48%; C-I, 43° C.; N-I, [−10° C.]

Yield, 59%; C-I, 99° C.; N-I, [88° C.]

Examples of materials and devices embodying the invention (in the second and third aspects above) will now be described by way of example only with reference to the accompanying drawings wherein.

The display of FIGS. 1 to 4 comprises a cell 1, formed of two, front and back, glass slides 2, 3 respectively, spaced about 7 m apart by a spacer 4 all held together by an epoxy resin glue. A liquid crystal material 12 fills the gap between the slides 2, 3 and the spacer 4. In front of the front glass slide 2 is a front polariser 5 arranged with its axis of polarisation axis horizontal. A reflector 7 is arranged behind the slide 3. A rear polariser 6 or analyser is arranged between the slide 3 and reflector 7.

Figure 3:
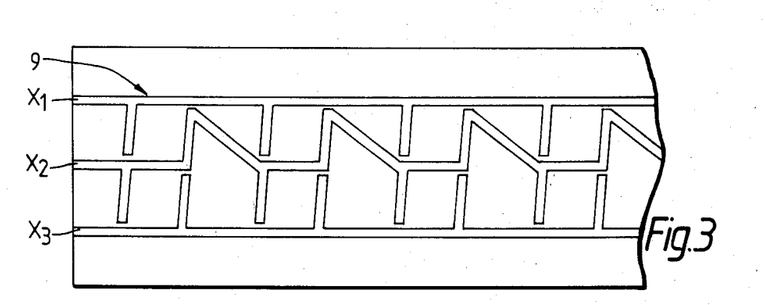
FIG. 3 shows a rear electrode configuration for FIG. 1.
Figure 4:
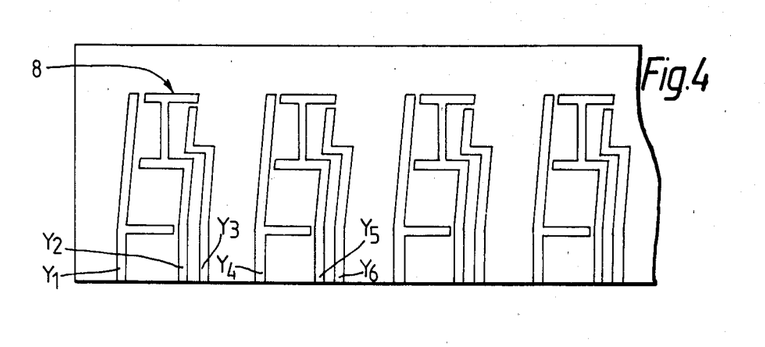
FIG. 4 shows a front electrode configuration for FIG. 1.

Electrodes 8, 9 of tin oxide typically 100 Å thick are deposited on the inner faces of the slides 2, 3 as a complete layer and etched to the shapes shown in FIGS. 3, 4. The display has seven bars per digit 10 plus a decimal point 11 between each digit. As shown in FIG. 3 the rear electrode structure is formed into three electrodes $x_1$, $x_2$, $x_3$. Similarly the front electrode structure is formed into three electrodes per digit and decimal point $y_1$, $y_2$, $y_3$ . . . . Examination of the six electrodes per digit shows that each of the eight elements can independently have a voltage applied thereto by application of suitable voltage to appropriate x, y electrodes.

Figure 1:
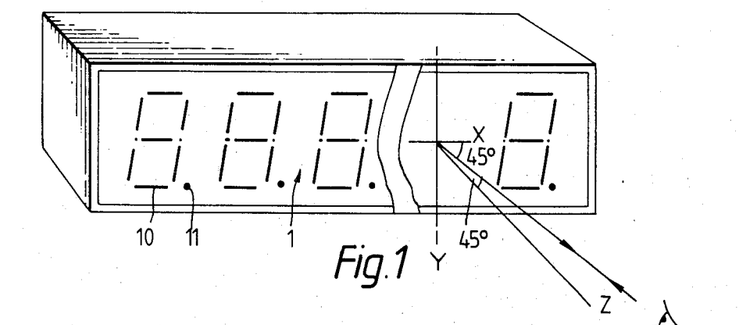
FIG. 1 is a sectional view of a twisted nematic digital display.
Figure 2:
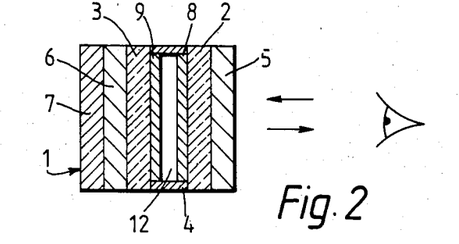
FIG. 2 is a sectional view of the display shown in FIG. 1.

Prior to assembly the slides 2, 3 bearing the electrodes are cleaned then dipped in a solution of 0.2% by weight of polyvinyl alcohol (PVA) in water. When dry, the slides are rubbed in a single direction with a soft tissue then assembled with the rubbing directions orthogonal to one another and parallel to the optical axis of the respective adjacent polarisers, i.e. so that t the polarisers are crossed. When the nematic liquid crystal material 12 is introduced between the slides 2, 3 the molecules at the slide surfaces lie along the respective rubbing directions with a progressive twist between the slides.

When zero voltage is applied to the cell 1 light passes through the front polariser 5, through the cell 1 (whilst having its plane of polarisation rotated 90°) through its rear polariser 6 to the reflector 7 where it is reflected back again to an observer (shown in FIG. 1 at an angle of 45° to the axis Z normal to axes X and Y in the plane of the slides 2, 3). When a voltage above a threshold value is applied between two electrodes 8, 9 the liquid crystal layer 12 loses its optical activity, the molecules being re-arranged to lie perpendicular to the slides 2, 3, i.e. along the axis Z. Thus light at the position does not reach the reflector 7 and does not reflect back to the observer who sees a dark display of one or more bars of a digit 10.

Figure 5:
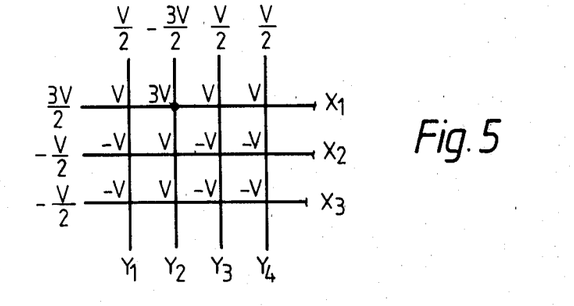
FIGS. 5, 6, 7 show schematic views of the device of FIGS. 1 to 4 with typical addressing voltages.
Figure 6:
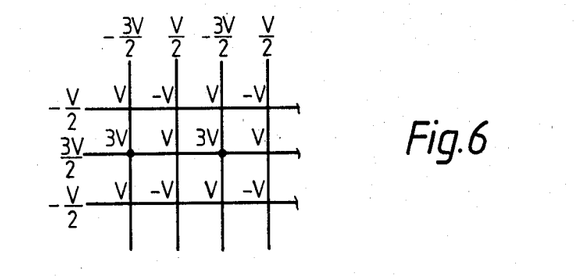
Figure 7:
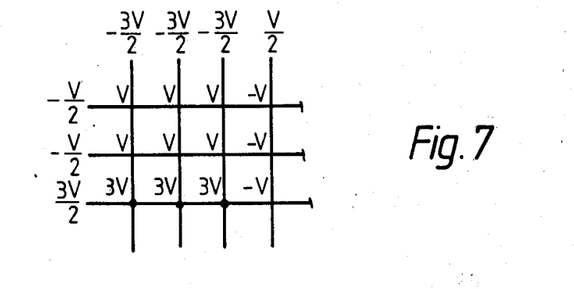

Voltages are applied as follows as shown in FIGS. 5, 6 and 7 for three successive time intervals in a linescan fashion. An electrical potential of 3 V/2 is applied to, i.e. scanned down, each x electrode in turn whilst −V/2 is applied to the remaining x electrodes. Meanwhile −3 V/2 or V/2 is applied to the y electrodes. A coincidence of 3 V/2 and −3 V/2 at an intersection results in a voltage 3 V across the liquid crystal layer 12. Elsewhere the voltage is V or −V. Thus by applying −3 V/2 to appropriate y electrodes as 3 V/2 is scanned down the x electrodes selected intersections are turned ON as indicated by solid circles. The electric voltage V is an ac signal of e.g. 100 Hz square wave, and the sign indicates the phase.

It will be apparent to those skilled in the art that the device shown in FIGS. 1 to 7 is a multiplexed display because the electrodes are shared between ON and OFF intersections or display elements.

A Material embodying the second aspect of the invention which is suitable for use as the material 12 in the above device is in Table 2 as follows (Mixture 1).

TABLE 3

| Mixture 1 | |
|---|---|
| Compound | Weight percentage |
| C$_2$H$_5$—⬡—⬡—CN | 15 |
| n-C$_4$H$_9$—⬡—⬡—CN | 23 |
| C$_2$H$_5$—(H)—COO—⬡—⬡—CN | 12 |
| n-C$_5$H$_{11}$—(H)—⬡—⬡—CN | 10 |
| ZLI 1052* | 30 |
| n-C$_5$H$_{11}$—(A)—CH$_2$O—⬡—OC$_4$H$_9$—n | 10 |

*ZLI 1052 is commercially available from E Merck Co and is a mixture of esters of the form R'$_1$—⬡—COO—⬡—R'$_2$ where R'$_1$ = n-alkyl and R'$_2$ = n-alkoxy.

Small amounts of a cholesteric material may be added to the nematic material to induce a preferred twist in the molecules in the liquid crystal layer. This and the use of appropriate slide surface treatment removes the problems of display patchiness as taught in UK Pat. Ser. Nos. 1,472,247 and 1,478,592.

Suitable cholesteric materials are:
C 15 about 0.1–0.5% by weight and CB 15 about 0.1% to 0.05% by weight.

Small amounts of pleochroic dye may be added to enhance the display contrast, e.g. one of the anthroquinone dyes described in UK patent specification No. 2011940A.

In another embodiment mixtures embodying the second aspect of the invention may be used in a Freedericksz effect cell. Such a cell may be constructed by sandwiching the liquid crystal material between glass slides having electrode films deposited on their inner surfaces as in the above device. However, in this case the polarisers are not necessary, the glass slide inner surfaces are treated with a coating of lecithin and the liquid crystal material is a negative material whose molecules are aligned in the OFF state perpendicular to the slide substrates (homeotropic texture) by the lecithin coating. Application of an appropriate electric field across the material in the ON state re-arranges the molecules parallel to the slide surfaces (homogeneous texture). A pleochroic dye may be incorporated in the liquid crystal material to enhance the contrast between the ON and OFF states.

A Freedericksz effect cell made in the above way may incorporate Mixture 2 below, the cell spacing being 10 μm.

TABLE 4

| Mixture 2 | |
|---|---|
| Compound | Weight percentage |
| n-C$_5$H$_{11}$—(H)—CH$_2$O—⬡—C$_4$H$_9$-n | 7 |
| n-C$_5$H$_{11}$—(H)—CH$_2$O—⬡—C$_5$H$_{11}$-n | 7 |
| ZLI 1052 | 80 |
| C$_2$H$_5$—(H)—COO—⬡(CN)(CN)—OOC—(H)—C$_2$H$_5$ | 6 |
| Compound A | |

The preparation of Compound A is described in UK patent application No. 7934129. 1.2% by weight of a known pleochroic due e.g. 1,5-bis-4'-n-butyl-phenylaminoanthraquinone may be added to Mixture 2 to give a dyed mixture. (Mixture 2A)

When a voltage is applied across the cell, the colour changes from a weakly absorbing state to a strongly absorbing state.

In an alternative embodiment of the invention a (cholesteric-to-nematic) phase change effect device incorporates a material as defined above.

A cell is prepared containing a long helical pitch cholesteric material sandwiched between electrode-bearing glass slides as in the twisted nematic cell described above. However the polarisers and surface preparations for homogeneous alignment, e.g. treatment of the glass slide surfaces with SiO, are not used in this case.

If the glass slides are untreated and the liquid crystal material has a positive dielectric anisotropy ($\Delta\epsilon$) the liquid crystal material is in a twisted focal conic molecular texture in the OFF state which scatters light. The effect of an electric field applied between a pair of electrodes on the respective inner surface of the glass slides is to convert the region of liquid crystal material between the electrodes into the ON state which is a homeotropic nematic texture which is less scattering than the OFF state. This is a 'negative contrast' type of phase change effect device.

If the inner glass slide surfaces are treated, e.g. with a coating of lecithin, to give alignment perpendicular to those surfaces, and the liquid crystal material has $\Delta\epsilon$ negative the material in the OFF state is in a homeotropic texture which has little scattering effect on incident light. If an electric field is applied between a pair of electrodes on the respective inner surfaces of the glass slides the region of liquid crystal material between the electrodes is converted to a twisted homogeneous texture which scatters light (the ON state). This is a 'positive contrast' type of phase change effect device.

The contrast between the two states in each case may be enhanced by the addition of a small amount of a suitable pleochroic dye (e.g. 1% by weight of 1,5-bis-4'-n-butylphenylaminoanthraquinone in the case where $\Delta\epsilon$ is positive) to the liquid crystal material.

A suitable positive dielectric anisotropy material embodying the invention for use in a phase change effect device is:

TABLE 5

Mixture 3

| Material | Weight percentage |
|---|---|
| Mixture B | 60% |
|  | 10% |
| R$_C$O—⟨⟩—⟨⟩—CN(R$_C$=(+)-2-methylbutyl) |  |
| C15 (known) |  |
| ZLI 1052 | 20% |
|  | 10% |
| n-C$_5$H$_{11}$—⟨H⟩—CH$_2$O—⟨⟩—C$_4$H$_9$-n |  |

A suitable negative dielectric anisotropy material embodying the invention for use in a phase change effect device, Mixture 4, is as follows:

TABLE 6

Mixture 4

| Compound | Weight percentage |
|---|---|
| ZLI 1052 | 80% |
|  | 5% |
| n-C$_5$H$_{11}$—⟨H⟩—CH$_2$O—⟨⟩—C$_4$H$_9$—n |  |

TABLE 6-continued

Mixture 4

| Compound | Weight percentage |
|---|---|
| n-C$_5$H$_{11}$—⟨H⟩—CH$_2$O—⟨⟩—C$_5$H$_{11}$—n | 6% |
| C$_2$H$_5$—⟨H⟩—COO—⟨⟩(CN)(CN)—OOC—⟨H⟩—C$_2$H$_5$ | 8% |
| R$_C$—⟨⟩—⟨⟩—COO—⟨⟩—R$_C$ | 1% |

We claim:

1. A liquid crystal compound exhibiting a low dielectric anisotropy and having a structural formula:

where R$_1$ is an alkyl group, R$_2$ is a group containing an alkyl group R and is either an alkyl group R, an alkoxy group OR, an alkylcarbonyloxy group OCOR or an alkoxycarbonyloxy group OCOOR, R$_1$ and R containing up to 18 carbon atoms, is a trans-1,4 disubstituted cyclohexane ring or a 1,4-disubstituted bicyclo(2,2,2)octane ring and Ar is a 1,4 disubstituted benzene ring a 3-fluoro-1,4 disubstituted benzene ring or a 2,6 disubstituted naphthalene ring

2. A liquid crystal compound as claimed in claim 1 and wherein $R_1$ is an n-alkyl group having up to 10 carbon atoms and $R_2$ is an n-alkyl or n-alkoxy group having up to 10 carbon atoms.

3. A liquid crystal compound as claimed in claim 1 and wherein the group is a trans-1,4 disubstituted cyclohexane ring.

4. A liquid crystal compound as claimed in claim 3 and wherein the group Ar is a 1,4 disubstituted benzene ring

5. A liquid crystal compound as claimed in claim 3 and wherein the group Ar is a 3-fluoro-1,4 disubstituted benzene ring 6. A liquid crystal compound as claimed in claim 3 and wherein the group Ar is a 2,6 disubstituted naphthalene ring 7. A liquid crystal compound as claimed in claim 2 and wherein the group is a bicyclo(2,2,2)octane ring.

8. A liquid crystal compound as claimed in claim 7 and wherein the group Ar is a 1,4 disubstituted benzene ring.

9. A liquid crystal material comprising a mixture of liquid crystal compounds and wherein the improvement comprises at least one of said compounds being a compound as claimed in claim 1.

10. A liquid crystal electro-optic display device including two dielectric substrates at least one of which is optically transparent, a layer of liquid crystal material sandwiched between the substrates and electrodes on the inner surfaces of the substrates to enable an electric field to be applied across the layer of liquid crystal material to provide an electro-optic effect therein, wherein the improvement comprises said material being a material as claimed in claim 9.

* * * * *